United States Patent [19]

Raaf

[11] Patent Number: 4,559,224

[45] Date of Patent: Dec. 17, 1985

[54] TOOTH AND MOUTH CARE AGENT

[75] Inventor: Helmut Raaf, Schönblick, Fed. Rep. of Germany

[73] Assignee: Blendax-Werke R. Schneider GmbH & Co., Mainz, Fed. Rep. of Germany

[21] Appl. No.: 703,426

[22] Filed: Feb. 20, 1985

Related U.S. Application Data

[62] Division of Ser. No. 597,849, Apr. 9, 1984, Pat. No. 4,525,343.

[30] Foreign Application Priority Data

Apr. 25, 1983 [DE] Fed. Rep. of Germany ....... 3314895

[51] Int. Cl.$^4$ .......................... A61K 7/16; A61K 7/22
[52] U.S. Cl. ........................................ 424/54; 424/49; 424/58
[58] Field of Search ..................................... 424/49–58

[56] References Cited

U.S. PATENT DOCUMENTS 4,525,343  6/1985  Raaf ..................................... 424/54

FOREIGN PATENT DOCUMENTS 54-154535  12/1979  Japan .

OTHER PUBLICATIONS

Derwent AN 80-04470c/03 XRAM C80-C04470 of Sunstar Hamigaki, K.
Japan 54154535 79.12.05 Saccharine-Free Dentifrice Compn. Contg. Neohesperidin and Narangin Dihydrochalcones and Ascorbic Acid.
Incavo C.A. 82 #110352s (1975) Dihydrochalcones as Sweetening Agents.
Lambev C.A. 93 #197805r (1980) Capillary Strengthening Antiinflammatory Action of Narangin.
Ramaswamy C.A. 77 #43732x (1972) Antibacterial Action of Citrus Bioflavanoids.
Coustou C.A. 78 #115243j (1973) of Fr. M7953 Bioflavoids such as Hesperidin Decrease Capillary Permeability.
Robbins C.A. 83 #172845j (1975) of U.S. Pat. No. 3,903,266, Sep. 2, 1975.
Matsumura C.A. 92 #99562a (1980) of Jpn 79101412, Vit. P. from Hesperidin.

*Primary Examiner*—Shep K. Rose
*Attorney, Agent, or Firm*—Connolly and Hutz

[57] ABSTRACT

The efficacy of tooth and mouth care agents, especially in reducing the inflammation and bleeding tendency of the gums, is increased by addition of hesperidin.

4 Claims, No Drawings

TOOTH AND MOUTH CARE AGENT

This is a division of application Ser. No. 597,849 filed Apr. 9, 1984 now U.S. Pat. No. 4,525,343.

The present invention concerns a new agent for care of the teeth and the mouth maintaining the gums in a healthy condition, inhibiting the formation of dental plaque and thus particularly eliminating the causes of gingival diseases.

Tooth and mouth care agents with such purposes have been known and are also commercially available since a long time.

For incorporation into such toothpastes, different active ingredients have been suggested.

It has now been found that by addition of hesperidin, preferably in a quantity between 0.05 and 2.5% by weight, preferably 0.1 to 1.0, particularly 0.1 to 0.5% by weight, calculated on the total composition, to the tooth and mouth care agent according to the invention, an excellent gum-conditioning effect, particularly concerning the treatment and prevention of gingival bleeding, is achieved.

This effect even may be increased by a synergistic effect if hesperidin is used in the tooth and mouth care agents together with urea. The effect of urea which has proven its use in practice is known. The prior art for this substance not only states that it has a caries-prophylactic effect and prevents the formation of dental calculus (cf. Journal of Periodontology, Vol. 37, (1966), pp 20–33), but it also has a keratinizing effect, i.e., when present in sufficient concentration in tooth and mouth care agents, it strengthens the gums, which is demonstrated by a significant increase in the keratinization-index.

It was, however, surprising that the efficacy of hesperidin, which is already surprising as such, can still be increased synergistically.

A particularly favorable effect was obtained when a toothpaste containing at least 5 to 15% by weight of urea, preferably 8% by weight, with approx. 0.1% to approx. 1%, preferably approx. 0.1 to 0.5% by weight, of hesperidin, related to the total composition, was subjected to a clinical investigation.

As known, hesperidin is a flavanone of the structure 3′,5,7-trihydroxy-4′-methoxyflavanone-7-[6-($\beta$-L-rhamnosido)-D-glucoside], which may be prepared from the peels of unripe oranges (cf. Römpp's Chemie-Lexikon, 7th edition, p. 1458).

The name hesperidin does not only mean the glycoside itself, but also its pharmacologically active derivatives, particularly the esters, e.g. mono- and di-phosphoric ester, the ascorbate and its salts, whereby the indicated quantity is related in each case to hesperidin.

As already stated, the preferred quantity of hesperidin in the tooth and mouth care agent according to the invention amounts to approx. 0.05 to 2.5% by weight of the total composition; an optimum dosage is between approx. 0.1 and 1% by weight, e.g. 0.1 to 0.5% by weight of the total composition.

The optional proportion of urea in the tooth and mouth care agent according to the invention is preferably at least 5% by weight of the total composition; a particularly favorable effect has been found with a combination of 8% urea with 0.2% by weight of hesperidin. Generally, the urea content does not exceed 15% by weight, preferably 10% by weight, of the total composition.

Although in principle every suitable application of a tooth and mouth care agent containing urea and hesperidin may be used, e.g. mouth spray and tooth powder, the preferred application is in a toothpaste or a mouthwash.

Such a toothpaste may be opaque or transparent, containing a suitable polishing agent with a refraction index corresponding to the refraction index of the carrier material.

A particularly appropriate toothpaste is described in the Luxembourgian Pat. No. 82,933; it contains as polishing agent calcium carbonate and at least 5% by weight urea, approx. 0.5% to 1.6% by weight of an alkaline salt of a higher fatty acid with about 12 to about 18 carbon atoms, it contains basically no synthetic surfactants, and has a pH value of at least 7.5 in the alkaline range, preferably between 7.5 and 9.5.

However, it is also possible to use toothpastes based on other substances, containing polishing agents such as e.g. alkali aluminum silicates, particularly those of the Zeolite Type A, described in European Pat. Nos. 2,690 and 3,023, various calcium phosphates such as dicalcium orthophosphate in the form of its dihydrate or water-free, tricalcium phosphate, calcium pyrophosphate, insoluble alkali metaphosphate, alumina, or alumina trihydrate, silica in various modifications, such as silica xerogels, hydrogels, or precipitated silicas, or synthetic plastic materials in powder form.

Naturally, polishing mixtures of the above mentioned substances may also be used, e.g. a mixture of calcium carbonate and synthetic Zeolite A in a ratio of approx. 1:1.

The proportion of polishing agent in the toothpastes according to the invention is preferably between approx. 20% and 60% by weight of the total composition.

As already indicated, a preferred embodiment of the present invention is to include hesperidin or a synergistic combination of urea and hesperidin in such toothpastes which contain only a small or no proportion of synthetic surface-active substances but may rather contain alkali salts of higher fatty acids, e.g. those of lauric acid, myristic acid, palmitic acid, stearic acid, or mixtures thereof, e.g. coconut fatty acids or tallow acids. Such salts of higher fatty acids are preferably present in a quantity of between approx. 0.5% and 1.5% by weight of the total composition.

However, it is also possible to use the surface-active compounds usually included in toothpastes in quantities up to approx. 2% by weight of the total composition, optionally in admixture with the above mentioned salts of fatty acids. Such synthetic surface-active substances are e.g. alkyl sulphates, alkyl ether sulphates, olefin sulphonates, sodium lauroly sarcosinate or ampholytic, nonionic, and cation-active compounds.

A summary of the compounds that may be included in toothpastes as well as of other substances commonly used in the production of tooth care agents and the production methods for these can be found in the monography of M. S. Balsam and E. Sagarin, "Cosmetics—Science and Technology", 2nd edition, Vol. I, pp 423–533 (1972), to which reference is made.

The same applies to moisturizing agents commonly used in toothpastes in a proportion between approx. 10% and approx. 35% by weight, e.g. glycerol, diols such as 1,4-butanediol or 1,2-propanediol, or sugar alcohols such as sorbitol, mannitol and xylitol, and polyglycols with low molecular weights, as well as to thickeners, of which the proportion in toothpastes amounts between approx. 0.25% and approx. 5% by weight of the total composition.

Preferred thickeners are carboxymethyl cellulose and its alkali salts, particularly sodium carboxymethyl cellulose, hydroxyalkyl celluloses such as hydroxymethyl cellulose and hydroxyethyl cellulose, methyl cellulose, natural gums such as tragacanth, caraya gum, guar gum, xanthan gum, and Irish moss, synthetic polyelectrolytes such as alkali salts of polyacrylic acids, as well as inorganic thickeners, e.g. colloidal magnesium aluminum silicate or colloidal silica.

Naturally, other substances may also be used in the tooth and mouth care agents according to the invention, particularly the well known caries-prophylactic fluorides, preferably in such a quantity that the concentration of fluorine (F) in the preparation is between approx. 0.05% and approx. 1% by weight, preferably 0.1% to 0.5% by weight of the preparation.

Suitable fluorine compounds are particularly the various salts of monofluorophosphoric acid, particularly sodium, potassium, lithium, calcium and aluminum mono- and difluorophosphates, as well as the various fluorides containing fluorine in ionically bound form, particularly alkali fluorides such as sodium, lithium, potassium and ammonium fluoride, stannous fluoride, manganese fluoride, copper fluoride, zirconium fluoride, and aluminum fluoride, as well as mixtures or addition products of these fluorides mutually or with other fluorine compounds, e.g. alkali manganese fluoride.

Organic fluorine compounds can also be successfully used, particularly the known addition products of long-chain amines or amino acids and hydrogen fluoride, monoethanolamine hydrofluoride, or monoethyl triethyl ammonium fluoride.

Additional substances which may be added to the tooth and mouth care preparations according to the invention are substances that prevent dental plaque formation, e.g. bisguanides known under the trade names "Chlorhexidine" or "Alexidine", 1,6-di-4'-(chlorophenyl diguanido)hexane or 1,6-di-(2-ethylhexyl diquanido)hexane or their preferably water-soluble salts; compounds to prevent the formation of dental calculus, such as hydroxyethane-1,1-diphosphonic acid or alkylene(tetramethylene phosphonic acids) and their water-soluble salts, allantoin, azulen, etc.

The following examples characterize the nature of the present invention and the advantageous effects thereof:

EXAMPLE 1

| Opaque Toothpaste | % by weight |
| --- | --- |
| Methyl hydroxyethyl cellulose | 1.00 |
| Calcium carbonate | 42.00 |
| Urea | 8.00 |
| Allantoin | 0.30 |
| Sodium laurate | 0.65 |
| Sodium benzoate | 0.30 |
| Methyl p-hydroxybenzoate | 0.15 |
| Saccharine sodium | 0.05 |
| Sorbitol, 70% | 8.00 |
| Hesperidin | 0.60 |
| Colloidal silica | 0.35 |
| Flavour composition | 1.00 |
| Water | 37.60 |

EXAMPLE 2

| Opaque toothpaste | % by weight |
| --- | --- |
| Urea | 6.00 |
| Sodium monofluorophosphate | 0.75 |
| Allantoin | 0.10 |
| Sodium stearate/laurate (1:1) | 0.70 |
| Sodium benzoate | 0.25 |
| Calcium carbonate | 40.00 |
| Methyl p-hydroxybenzoate | 0.15 |
| Sodium cyclamate | 0.10 |
| Calcium silicate | 0.50 |
| Hydroxyethyl cellulose | 1.10 |
| Sorbitol, 70% | 9.00 |
| Flavour composition | 1.00 |
| Hesperidin | 0.55 |
| Water | 39.80 |

EXAMPLE 3

| Opaque Toothpaste | % by weight |
| --- | --- |
| Calcium carbonate | 22.50 |
| Synthetic Zeolite A (according to European Patent No. 3,023; $Na_{12}(AlO_2)_{12}(SiO_2)_{12}.27\ H_2O$) | 17.50 |
| Glycerol | 3.50 |
| Carboxymethyl cellulose | 1.20 |
| Benzoic acid | 0.30 |
| Methyl p-hydroxybenzoate | 0.10 |
| Saccharine sodium | 0.05 |
| Sodium monofluorophosphate | 1.25 |
| Colloidal silica | 0.20 |
| Hesperidin ascorbate | 0.80 |
| Flavour mixture | 1.00 |
| Sodium lauryl sulphate, 86% | 1.20 |
| Water | 33.90 |

EXAMPLE 4

| Transparent toothpaste | % by weight |
| --- | --- |
| Carboxymethyl cellulose | 0.50 |
| Sodium benzoate | 0.15 |
| Polyethylene glycol 400 | 5.00 |
| Glycerol | 45.00 |
| Urea | 7.50 |
| Hesperidin monophosphate, sodium salt | 0.95 |
| Allantoin | 0.15 |
| Guajazulene | 0.05 |
| Saccharine sodium | 0.07 |
| Sodium lauroyl sarcosinate | 1.10 |
| Phenyl salicylate | 0.10 |
| Flavour composition | 1.00 |
| 10% blue dye mixture | 0.03 |
| Dehydrated silica gel (surface 290 m$^2$/g; average particle diameter 6 μm) | 20.00 |
| Water | 18.40 |

EXAMPLE 5

| Opaque Toothpaste | % by weight |
| --- | --- |
| Chlorhexidine digluconate | 0.10 |
| Hesperidin | 0.65 |
| Allantoin | 0.20 |
| Sodium fluoride | 0.30 |
| Alumina trihydrate | 25.00 |
| Zeolite A (according to European Patent No. 3,023; $Na_{12}(AlO_2)_{12}(SiO_2)_{12}.27\ H_2O$) | 15.00 |
| Medical soap (German Pharmacopoe No. 6) | 0.70 |

| Opaque Toothpaste | % by weight |
|---|---|
| Sodium sulphoricinoleate | 0.30 |
| Hydroxyethyl cellulose | 1.05 |
| n-Propyl p-hydroxybenzoate | 0.15 |
| Methyl p-hydroxybenzoate | 0.15 |
| Sodium benzoate | 0.15 |
| Saccharine sodium | 0.05 |
| Glyerol | 8.50 |
| Sorbitol, 70% | 7.50 |
| Flavour composition | 1.20 |
| Water | 39.00 |

EXAMPLE 6

| Mouthwash Concentrate | % by weight |
|---|---|
| Diphosphoric ester of hesperidin, sodium salt | 1.60 |
| Flavour composition | 3.50 |
| Nonionogenic emulgator | 6.00 |
| 1,2-propyleneglycol | 7.00 |
| Sorbitol, 70% | 5.00 |
| 1,2-Propyleneglycol monomethyl ether | 17.00 |
| Sodium cyclamate | 0.30 |
| Allantoin | 0.25 |
| Azulene | 0.05 |
| Desalted water | 59.30 |

Before use, the concentrate is diluted with water in the ratio 1:10.

We claim:

1. Tooth and mouth care preparations in the form of toothpaste, mouthwash, mouth spray or tooth powder, containing hesperidin as the essential active ingredient in an amount effective to treat and prevent gingival bleeding.

2. Tooth and mouth care preparation according to claim 1, characterized in that it contains 0.05% to 2.5% by weight of hesperidin, calculated on the total composition.

3. Tooth and mouth care preparation according to claim 2, characterized in that it contains 0.1% to 1.0% by weight of hesperidin, calculated on the total composition.

4. Tooth and mouth care preparation according to claim 1, in the form of a toothpaste on aqueous basis, containing calcium carbonate as the only or predominant polishing agent, 0% to 15% by weight of urea, 0.5% to 1% by weight, related to the total composition, of an alkali salt of $C_{12}$ to $C_{22}$ fatty acids, having a pH value above 7.5, characterized in that it contains hesperidin.

* * * * *